United States Patent
Folgero et al.

(10) Patent No.: US 10,139,215 B2
(45) Date of Patent: Nov. 27, 2018

(54) PERMITTIVITY MEASUREMENTS OF LAYERS

(71) Applicant: TeCom AS, Bergen (NO)

(72) Inventors: Kjetil Folgero, Hjellestad (NO); Jan Kocbach, Bergen (NO); Kjetil Haukalid, Espeland (NO)

(73) Assignee: TeCom AS, Bergen (NO)

( * ) Notice: Subject to any disclaimer, the term of this patent is extended or adjusted under 35 U.S.C. 154(b) by 0 days.

(21) Appl. No.: 15/323,431

(22) PCT Filed: Jul. 2, 2015

(86) PCT No.: PCT/NO2015/050122
§ 371 (c)(1),
(2) Date: Jan. 2, 2017

(87) PCT Pub. No.: WO2016/003291
PCT Pub. Date: Jan. 7, 2016

(65) Prior Publication Data
US 2017/0160069 A1    Jun. 8, 2017

(30) Foreign Application Priority Data

Jul. 2, 2014 (GB) .................................. 1411807.9
Jul. 2, 2014 (NO) .................................. 20140850

(51) Int. Cl.
*G01N 33/18* (2006.01)
*G01B 7/06* (2006.01)
(Continued)

(52) U.S. Cl.
CPC .............. *G01B 7/06* (2013.01); *G01N 27/04* (2013.01); *G01N 27/06* (2013.01); *G01N 33/18* (2013.01)

(58) Field of Classification Search
CPC ........... G01B 7/06; G01N 27/04; G01N 27/06
See application file for complete search history.

(56) References Cited

U.S. PATENT DOCUMENTS 5,381,694 A    1/1995  Glynn
6,198,293 B1   3/2001  Woskov et al.
(Continued)

FOREIGN PATENT DOCUMENTS

EP    2561339 A1   2/2013
GB    2376074 A    12/2002
(Continued)

OTHER PUBLICATIONS

English language Abstract of RU 2203482 C2.
(Continued)

*Primary Examiner* — Giovanni Astacio-Oquendo
*Assistant Examiner* — Alvaro Fortich
(74) *Attorney, Agent, or Firm* — Hershkovitz & Associates, PLLC; Abe Hershkovitz

(57) ABSTRACT

A system and method that permits measuring properties and thickness of a dielectric layer, particularly a dielectric layer close to a pipeline wall, and more particularly fluids flowing inside a pipe is provided. The present invention attains the above described objective by a system comprising a sensor operating in a material characterization mode in a first frequency range and a sensor operating in a thickness characterization mode in a second frequency range, and a method for operating said system.

25 Claims, 6 Drawing Sheets

(51) Int. Cl.
  G01N 27/04 (2006.01)
  G01N 27/06 (2006.01)

(56) References Cited

U.S. PATENT DOCUMENTS

| | | | |
|---|---|---|---|
| 6,831,470 B2 | 12/2004 | Xie et al. | |
| 7,607,358 B2 * | 10/2009 | Atkinson | G01F 1/34 73/861.12 |
| 2003/0011386 A1 | 1/2003 | Xie et al. | |
| 2008/0272789 A1 * | 11/2008 | San Martin | G01V 3/24 324/355 |
| 2009/0204346 A1 * | 8/2009 | Xie | G01F 1/66 702/45 |
| 2010/0064820 A1 | 3/2010 | David et al. | |
| 2011/0271769 A1 * | 11/2011 | Kippersund | G01F 1/42 73/861.28 |
| 2013/0033272 A1 | 2/2013 | Folgeroe et al. | |
| 2013/0047709 A1 * | 2/2013 | Xie | G01F 1/36 73/61.45 |
| 2013/0327154 A1 | 12/2013 | Xie et al. | |
| 2014/0298900 A1 * | 10/2014 | Clarke | E21B 49/00 73/152.55 |

FOREIGN PATENT DOCUMENTS

| | | |
|---|---|---|
| NO | 19971025 | 9/1998 |
| RU | 2203482 C2 | 4/2003 |
| WO | WO 2011/133046 A1 | 10/2011 |

OTHER PUBLICATIONS

English language translation of NO 19971025.
International Search Report dated Oct. 22, 2015 in PCT/NO2015/050122.
International Preliminary Report on Patentability dated Jan. 3, 2017 in PCT/NO2015/050122.
Mahmoud Meribout et al., "Interface Layers Detection in Oil Field Tanks: A Critical Review", Expert Systems for Human, Materials and Automation, Ch. 10, (2011), p. 6.
K. Folgerøand T. Tjomsland "Permittivity measurement of thin liquid layers using open-ended coaxial probes" Measurement, Science & Technology, vol. 7, 1996, pp. 1164-1173.
K. Folgerø "Coaxial sensors for broad-band complex permittivity measurements of petroleum fluids", Dr. Science. Dissertation, 1996.
K. Folgerø, A. L. Tomren, S. Frøyen "Permittivity calculator. Method and tool for calculating the permittivity of oils from PVT data", 30th Int. North Sea Flow Measurement Workshop, St. Andrews, Oct. 2012.
K. Haukalid, K. Folgerø "Measurements of water conductivity in oil continuous emulsions", 10th Int Conf on Electromagnetic Interaction with Water and Moist Substances, Weimar, Germany, Sep. 25-27, 2013.
J. Hilland, "Simple sensor system for measuring the dielectric properties of saline solutions," Measurement Science and Technology, vol. 8, No. 8, 1997, pp. 901-910.
T. Jakobsen and K. Folgerø "Dielectric measurements of gas hydrate formation in water-in-oil emulsions using open-ended coaxial probes" Measurement, Science & Technology, vol. 8, 1997, pp. 1006-1015.
Baker-Jarvis J., Janezic M. D., Domich P. D. and Geyer R. G. "Analysis of an open-ended coaxial probe with lift-off for nondestructive testing," IEEE Trans Instrum. Meas., vol. 43, No. 5, 1994, pp. 711-718.
Gerardo G. Clemeña "Short-Pulse Radar Methods" in "Handbook on Nondestructive Testing of Concrete," edited by V. M. Malhotra, Nicholas J. Carino, by CRC Press LLC, 2004, pp. 13-1-13-21.
A. Peyman, C. Gabriel and E. H. Grant, "Complex permittivity of sodium chloride solutions at microwave frequencies," Bioelectromagnetics, vol. 28, No. 4, 2007, pp. 264-274.
A. H. Sihvola and Institution of Electrical Engineers, "Electromagnetic Mixing Formulas and Applications," Institution of Electrical Engineers, 1999, pp. 45-47 and 161-163.
M. T. Ghasr, D. Simms, and R. Zoughi, "Multimodal solution for a waveguide radiating into multilayered structures—Dielectric property and thickness evaluation," Instrumentation and Measurement, IEEE Transactions on, vol. 58, No. 5, 2009, pp. 1505-1513.
Jannier B. et al., Application of microwave reflectometry to disordered petroleum multiphase flow study, Measurement Science and Technology, IOP, Bristol, GB, vol. 24, No. 2, Jan. 18, 2013, p. 25304.
Extended European Search dated Jan. 12, 2018 by the European Patent Office in related European Patent Application No. 15814128.3.

* cited by examiner

PERMITTIVITY MEASUREMENTS OF LAYERS

TECHNICAL FIELD

The invention relates to measurement in general and more specifically a system and a method for characterizing layers close to a pipeline wall.

BACKGROUND ART

Deposition of wax, hydrate, asphaltenes and scale during production and transportation of hydrocarbons is causing considerable economic losses to petroleum industries. Moreover, break-through of formation or injection water can also create problems. These economical losses arise through the cost of chemicals, reduced production, equipment failure, and so on. Flow assurance is thus becoming an increasing challenge as depth and step-out distances to new oil and gas fields are increasing in order to exploit more outlying fossil fuel reserves. Systems for monitoring the flow, and to detect and characterize crystallization within the flow and deposition on the pipe wall, are therefore wanted by the industry.

This invention describes a method and apparatus for monitoring and characterizing multiphase flow in a pipeline, with emphasis on characterization of deposit layers and liquid films on the inside wall of a pipeline. The term characterization refers to determining physical properties and thickness of the layer material.

One background prior art reference is Norwegian Application NO19971025 that uses a device for measurement of a coefficient of reflection for high frequency waves in fluids as well as a method for determining water contents in multiphase pipe flow using that device. Another background reference is International Published Application WO2011133046 A1 (related to EP2561339A1 and US20130033272), which describes a method for measuring deposit layers on an inside wall of a pipeline. These inventions are applicable for characterizing the layers close to the pipe wall, but the problem is that these inventions do not assist in determining the layer thickness.

The background Published Application US2010064820 regards measurement of a multiple-phase fluid in a pipe. However, this document discloses a method that requires two sensors for measurement and cannot be used for thicknesses greater than the sensitivity or penetration depth of the largest probe.

Background Issued U.S. Pat. No. 6,198,293 discloses a method and apparatus for thickness measurement using microwaves. However, the method disclosed requires prior knowledge of the permittivity of the material to be measured.

Background Issued U.S. Pat. No. 5,381,694 A describes a method for measuring thickness of ice layers with electromagnetic waves. However, this invention considers ice layers of several wavelengths of thickness.

Finally, reference should also be made to Published Application US 2009/0204346, relating to measurements of a multiphase flow in a pipe.

As illustrated by the references above, known techniques for permittivity measurement of layers are used for either measuring the thickness of the layer by assuming a known layer permittivity or measuring the permittivity of the layer by assuming a known layer thickness. Compared to known techniques for permittivity measurement of layers, the invention makes it possible to determine both layer thickness and layer permittivity.

SUMMARY OF THE INVENTION

An object of the present invention is to provide a system and method that permits measuring properties including thickness of layers and fluid films, particularly layers and fluid films close to a pipeline wall, and more particularly, fluids flowing inside a pipe. The fluid film may be either stationary or flowing, and the fluid behind the layer or film (which is referred to as the backing material) may be either stationary of flowing. Possible layers include deposits of wax, scale, asphaltenes or hydrates. Possible liquid films include mixtures of water and oil, mixtures of water and alcohols, and mixtures of particles in liquid. The dielectric layer can be a non-uniform layer. The layer can also be made up of several sub-layers. The backing material may comprise several layers or non-uniform materials, and may refer to fluids, solids and mixtures thereof.

Characteristic properties and parameters that are important to measure are, e.g., the conductivity and salinity of water, the water amount and water-in-liquid fraction, hydrate presence in the flow, hydrate deposits on the pipe wall, water and gas content in hydrate layers, porosity of hydrate deposits, presence of wax particles in flow, wax deposits on the pipe wall, scale deposits on the pipe wall, asphaltene deposits on the pipe wall, and the thickness of deposit and fluid layers, The present invention teaches a monitoring technique for characterization and thickness measurement of deposits and fluid layers. The term layers refers to deposits, fluid layers, fluid films, liquid layers and similar build-up of substances. The inventive characterization comprises measuring the permittivity, or related quantity, of the layer and calculating other characteristics from the permittivity by employing appropriate models. Examples of characteristics that can be derived from the layer permittivity are water conductivity and salinity, water-in-liquid ratio, water content in hydrate deposit or slurry, hydrate porosity, etc. Alternatively, the characterization can be done directly on the measured quantity (measurand), which can for instance be the complex reflection coefficient (S11), input impedance or voltage.

These and other objects are achieved according to the invention by a method for characterizing a dielectric layer with a backing material or fluid behind the dielectric layer, the method comprising measuring a parameter in a first frequency range, measuring a parameter in a second frequency range, estimating a permittivity in the first frequency range from the measured parameter in the first frequency range, estimating a permittivity in the second frequency range by combining an application based model with the estimated permittivity in the first frequency range, and estimating thickness of the dielectric layer from the measured parameter in the second frequency range. The first frequency range is a material characterization frequency range wherein reflections from an interface between the sensor and the dielectric layer is dominating the measurements, and the second frequency range is a thickness characterization frequency range wherein reflections from the interface between the dielectric layer and the backing material interfere with reflections from the interface between the sensor and the dielectric layer.

Further objects are achieved according to the invention by a method for a combined characterization of a dielectric layer and a backing material or fluid behind the dielectric, the method comprising characterizing the layer using the method described above in a first time period when the permittivity of the fluid or material behind the layer is known, measuring permittivity in a second time period when the permittivity of the fluid or material behind the layer is unknown, and estimating the permittivity of the fluid or material behind the layer from the measurement in the second time period.

Additional objects are achieved according to the invention by an apparatus for characterizing a dielectric layer with a backing material or fluid behind the dielectric layer using the method described above, the apparatus comprising a sensor measuring a parameter in a first frequency range, a sensor measuring a parameter in a second frequency range, wherein the first frequency range is a material characterization frequency range wherein reflections from the interface between the sensor and the dielectric layer is dominating the measurements, and wherein the second frequency range is a thickness characterization frequency range wherein reflections from the interface between the dielectric layer and the backing material interfere with reflections from the interface between the sensor and the dielectric layer.

A number of non-exhaustive embodiments, variants or alternatives of the present invention are defined by the appended claims.

The present invention attains the above-described objectives by the method for characterizing a dielectric layer with a backing material or fluid behind the dielectric layer, wherein the method comprises measuring a parameter in a first frequency range, measuring a parameter in a second frequency range, estimating a permittivity in the first frequency range from the measured parameter in the first frequency range, estimating a permittivity in the second frequency range by combining an application based model with the estimated permittivity in the first frequency range, estimating thickness of the dielectric layer from the measured parameter in the second frequency range, wherein the first frequency range is a material characterization frequency range wherein reflections from the interface between the sensor and the dielectric layer is dominating the measurements, and wherein the second frequency range is a thickness characterization frequency range wherein reflections from the interface between the dielectric layer and the backing material interfere with reflections from the interface between the sensor and the dielectric layer.

The system operates by measuring the complex reflection coefficient in a first frequency range using a first apparatus and measuring the complex reflection coefficient in a second frequency range using a second apparatus. In one embodiment of the invention, the same apparatus may be used for measuring the coefficients in both frequency ranges. Both the first apparatus and second apparatus are electromagnetic transceivers including a sensor element. The electromagnetic sensor may be either an open-ended coaxial probe, an open ended circular or rectangular waveguide, an open-ended evanescent mode waveguide, a horn antenna, slot antenna, slotted waveguide antenna or other antenna, a coplanar-waveguide, or a device based on another line measurement technique (such as a leaky waveguide). The sensor element can also be a resonator type sensor.

The technical differences of the present invention over NO19971025 is the use of a second operating mode for thickness estimation, and that other sensor types, technologies, topologies and implementations can be applied. This allows for determining a thickness estimate of layers close to a pipeline wall. Also, the present invention describes methods for estimating fluid parameters such as water conductivity, and water and hydrate content in the layer.

These effects provide in turn several further advantageous effects:
- it makes it possible to determine a thickness estimate of layers in a fluid flowing in a pipeline;
- it makes it possible to characterize the content of dielectric layers;
- it makes it possible to use the method for layers thicker than the reactive sensitivity or penetration depth of the largest probe; and
- in one aspect of the invention where the same apparatus is used for both frequency ranges, using a single probe reduces the complexities, cost and number of intrusions in the pipe.

BRIEF DESCRIPTION OF THE DRAWINGS

The above and further features of the invention are set forth with particularity in the appended claims, and together with advantages thereof, will become clearer from consideration of the following detailed description of an exemplary embodiment of the invention given with reference to the accompanying drawings.

The invention will be further described below in connection with exemplary embodiments which are schematically shown in the drawings, wherein.

REFERENCE NUMBERS

Figure 1A:
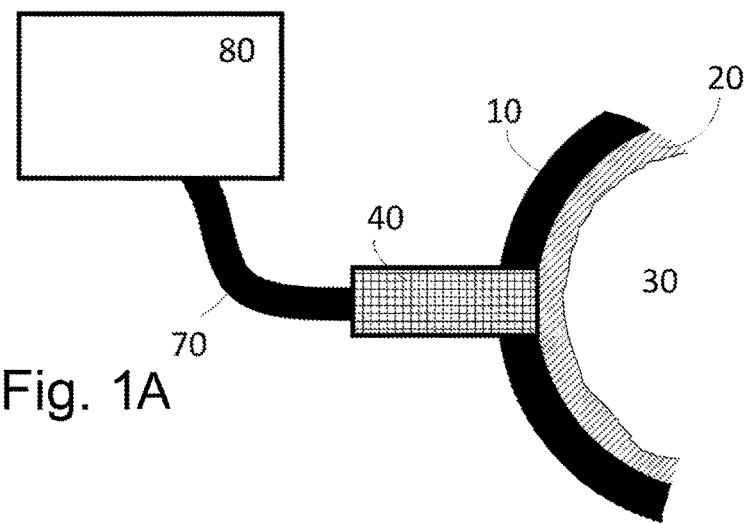
FIG. 1A shows an embodiment of an apparatus containing a transceiver and sensor mounted in pipeline.

10: pipe wall
20: deposit/layer/liquid film
25: liquid droplets
30: backing material
35: gas
36: liquid
40: sensor
41: open-ended coaxial probe sensor
42: waveguide horn antenna sensor
50: inner conductor of open-ended coaxial probe sensor
52: outer conductor open-ended coaxial probe sensor
60: dielectric material
70: connection cable
80: electronic unit/measurement instrument
101: measured real part of permittivity as a function of frequency for a semi-infinite thick layer
102: measured real part of permittivity as a function of frequency for a layer with finite thickness
103: simulated real part of permittivity as a function of frequency for a semi-infinite thick layer
104: measured real part of reflection coefficient as a function of frequency
105: simulated real part of reflection coefficient as a function of frequency for case with best fit to measurements
106: measured imaginary part of reflection coefficient as a function of frequency
107: simulated imaginary part of reflection coefficient as a function of frequency for case with best fit to measurements

DETAILED DESCRIPTION

Various aspects of the invention are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The invention will be further described in connection with exemplary embodiments which are schematically shown in the drawings.

FIG. 1A shows a sensor system for measuring the permittivity close to the inner wall of a pipeline. A sensor arrangement 40 is mounted in the wall of a pipeline 10 such that the sensing element or elements are in contact with the material and/or flow inside the pipe. The sensor arrangement can comprise several sensors, for example two sensors which are operated in different modes. In the following, the invention is described in the context of a sensor arrangement comprising a single sensor. The sensor is non-intrusive, or only intrudes a small distance into the flow, such that the sensor does not cause a pressure drop or disturbs the flow in other ways. Under certain flow conditions, the material or fluid in the pipeline will comprise a material or fluid 20 close to the wall and another material or fluid 30 behind the material or fluid 20. In the following, the fluid or material 20 close to the wall is referred to as a dielectric layer, and the fluid/material 30 as a backing material. The dielectric layer can comprise several sub-layers or be non-uniform, and the backing fluid or material can be non-uniform or comprise several layers. In one embodiment, the dielectric layer is a liquid layer, typically a mixture of water and oil, and the backing material is gas with liquid droplets. In another embodiment, the dielectric layer is a deposit and the backing material is a mixture of water, oil and gas.

An electronic unit 80, also referred to as a measurement instrument or transceiver, sets up an electromagnetic signal that propagates through a cable 70 to the sensor 40. In an alternative embodiment, the electronic unit 80 is connected directly to the sensor 40. The sensor sets up an electromagnetic signal that interacts with the materials or fluids inside the pipe, and reflects a signal back to the electronic unit which detects the reflected signal. In some embodiments, some of the signal propagates through the sensor and is partly transmitted to the same or another electronic unit.

Figure 2A:
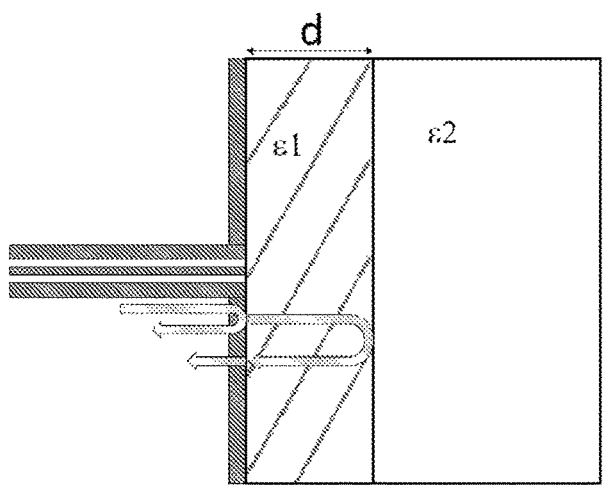
FIG. 2A shows a probe measuring a layer of thickness d and permittivity $\varepsilon_1$ backed by a material/fluid with permittivity $\varepsilon_2$.
Figure 2B:
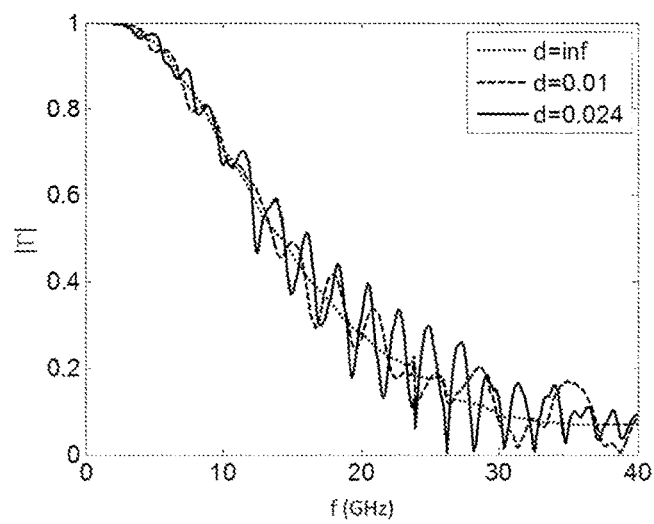
FIG. 2B shows simulated the reflection coefficient (absolute value) for some layer thicknesses.

A sensor can be operated in different operating modes depending on sensor configuration, frequency range of the applied signal, and characteristics of the materials or fluids inside the pipe. When operated in non-radiating mode, the electromagnetic field set up by the sensor only penetrates a small distance into the pipe. This distance or volume is referred to as the reactive region. Thus, the response of the sensor system will depend on the material properties inside the reactive region. When operated in radiating mode, the sensor will radiate electromagnetic energy and behave like an antenna. This energy will penetrate through the reactive region, into the radiative region and farther into the far field. In the far field, the electromagnetic signal propagates as a freely propagating wave with a well-defined relationship between E- and H-field. In the near field, which comprises the reactive region close to the sensor and the radiative region farther away from the sensor, the relationship between E- and H-field is more complex. As illustrated for the specific case of an open-ended coaxial probe in FIG. 2A, a radiated electromagnetic signal will be partly reflected from any impedance mismatches (e.g., interfaces between dielectric layers with different permittivity). If the impedance mismatch is within the reactive near field, the E- and H-field distribution around the aperture will be changed and result in a modified reflection coefficient from the probe material boundary (aka first interface). The size of the reactive region depends on the sensor type, technology and geometry, as well as the operating frequency. If the impedance mismatch is in the radiative near field or the far field, the reflected signals from the impedance mismatch will interfere with the reflections from the probe material boundary. This interference may be constructive or destructive depending on frequency, thickness, layer permittivity and backing material/fluid permittivity. The interference is typically observed as a ringing in the measured reflection coefficient (see FIG. 2B). In some cases, the interference can be negligible compared to the reflection from the first interface between the sensor and dielectric layer. In these cases, the sensor response will be approximately equal to the response when radiating into a semi-infinite dielectric material. This will be the case for instance if (a) the sensor is only partly radiating such that the energy in the radiated signal is small compared to the reflected signal at the first interface, (b) the impedance difference (contrast) between the dielectric layer and the backing material is low such that the reflected signal from the interface between the dielectric layer and the backing material is small, and/or (c) the dielectric losses in the dielectric layer is large and/or the layer thickness is high and/or the operating frequency is high such that the radiated and reflected signal is attenuated significantly compared to the reflection from the first interface.

Based on the description above, the following terminology is used throughout the description of the present invention.

The non-radiating operating mode refers to sensors operated such that the electromagnetic radiation from the sensor is negligible compared to reflected (or transmitted) energy from the sensor-dielectric layer interface. Thus, almost all energy is either reflected to the source or dissipated in the material close to the sensor. As the electromagnetic field distribution is limited to be within the reactive region of the sensor, the non-radiating operating mode is also referred to as the reactive operating mode.

The reactive sensitivity depth is defined as the region where the electromagnetic field surrounding the sensor is affected by the material permittivity when operating in non-radiating operating mode. Thus, material permittivity outside the reactive sensitivity depth will not affect the measured reflection (or transmission) coefficient when the sensor is operated in non-radiating operating mode.

The radiating operating mode refers to sensors operated such that electromagnetic energy radiated from the sensor is not negligible compared to the reflection from the sensor-dielectric layer interface.

The material characterization mode refers to a sensor operated in non-radiating operating mode, or a sensor operating in radiating mode, where reflections from the interface between the dielectric layer and the backing material is negligible compared with the reflection from the sensor-dielectric layer interface in the studied frequency range.

The thickness characterization mode refers to a sensor operating in a radiating operating mode where reflections from the interface between the dielectric layer and the backing material are not negligible compared with the reflection from the sensor-dielectric layer interface in the studied frequency range.

The material characterization frequency range refers to the frequency range where the sensor is in the material characterization mode, i.e., the frequency range where the sensor is not radiating, or reflections from the interface between the dielectric layer and the backing material do not interfere with reflections from the interface between the sensor and the dielectric layer.

The thickness characterization frequency range refers to the frequency range where the sensor is in the thickness characterization mode, i.e. the frequency range where the sensor is radiating, and reflections from the interface between the dielectric layer and the backing material interfere with reflections from the interface between the sensor and the dielectric layer.

In general, the thickness characterization frequency range differs from the material characterization frequency range. In embodiments where the sensor arrangement comprises a single sensor element, the thickness characterization frequency range is higher in frequency than the material characterization frequency range.

The permittivity of a dielectric material can be calculated from the measured amplitude and phase of the reflection coefficient at the given frequency when it is assumed that the dielectric material is uniform and has a semi-infinite thickness. When such a calculation method is used to calculate the permittivity of a non-uniform material and/or a material of finite thickness, the resulting calculated permittivity is frequently referred to as the apparent or effective permittivity. In this description of the present invention, the calculated apparent permittivity is referred to as measured permittivity or estimated permittivity. The permittivity is a frequency-dependent material parameter, and the frequency spectrum of the permittivity is determined by sweeping or stepping the reflection coefficient over the frequency range of interest. The permittivity can also be estimated from other parameters such as measured impedance.

This invention teaches a method for combined permittivity and thickness measurement:
the permittivity of the dielectric layer is estimated by measurements in the material characterization frequency range,
the permittivity in the thickness characterization frequency range is estimated by combining application based models with the estimated permittivity in the material characterization frequency range, and
the thickness of the dielectric layer is estimated from measurements in the thickness characterization frequency range. The thickness to be measured can be in the near field as well as the far field of the radiating sensor.

The application-based models refer to functions for estimating permittivity for varying frequency and material/fluid compositions. The permittivity depends on the composition of the materials/fluids, and can be estimated from theoretical models, numerical simulations, measured data, or combinations of these. Examples of such models are theoretical electromagnetic mixing formulas such as the formulas given by Bruggeman, Clausius-Mossotti et al. (Sihvola 1999), grid-fitting models based on laboratory calibration measurements, or systematic simulations.

Figure 1B:
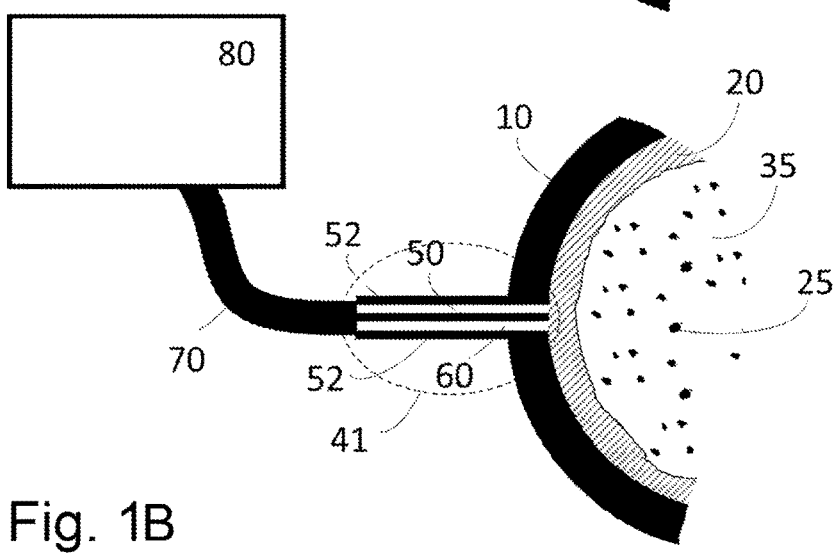
FIG. 1B shows an embodiment of an open-ended coaxial probe mounted in pipeline.

FIG. 1B shows a specific example wherein the sensor is an open-ended coaxial probe. The electromagnetic field of an open-ended coaxial probe, when operated in non-radiating operating mode, decays exponentially into the material under test, such that the reflection coefficient only senses materials close to the probe interface. The reactive sensitivity depth of an open-ended coaxial probe is approximately equal to the inner radius of the outer conductor of the coaxial probe. The open-ended coaxial probe will be non-radiating at lower frequencies and radiating at higher frequencies. Thus, the same sensor can be applied both for material and thickness characterization by operating the sensor over a broad frequency range.

Figure 1C:
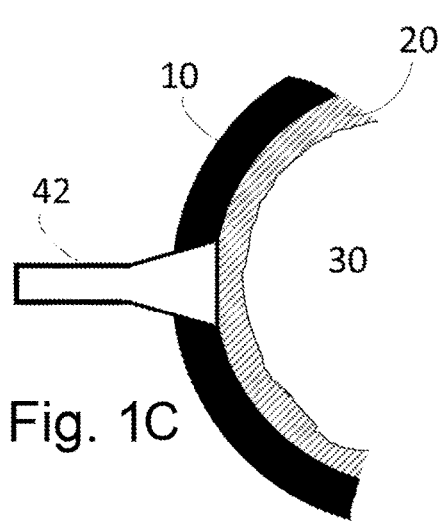
FIG. 1C shows an embodiment of a waveguide antenna mounted in pipeline.
Figure 1D:
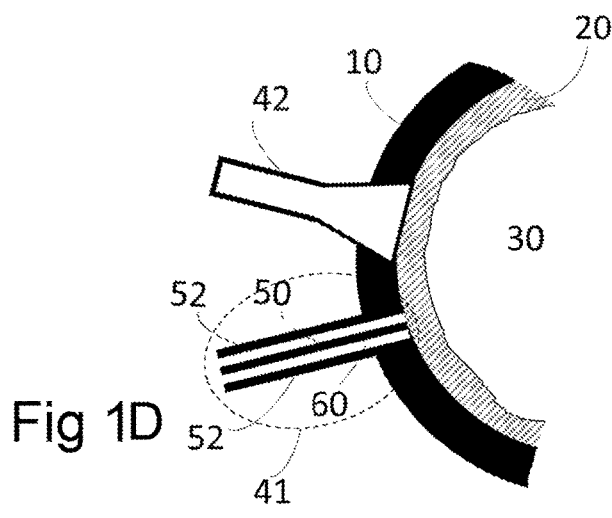
FIG. 1D shows an embodiment of a sensor arrangement comprising a waveguide antenna and an open-ended coaxial probe mounted in pipeline.

FIG. 1C shows another specific example, wherein the sensor is a waveguide antenna. The radiation from a waveguide antenna is much larger than the radiation from an open-ended coaxial probe, and this sensor is therefore particularly suited for operation in the thickness characterization range. One embodiment is a sensor arrangement combining an open-ended coaxial probe operating in material characterization frequency range and a waveguide antenna operating in thickness characterization frequency range. This is illustrated in FIG. 1D.

A special case of a waveguide antenna is an open-ended rectangular waveguide. An alternative embodiment is to use a horn antenna or an open-ended circular waveguide. The benefit of an open-ended waveguide compared to a standard waveguide horn antenna is that the interface area between the sensor and the layer is smaller, i.e. the footprint of the sensor is smaller. The benefit of using a horn antenna is that the radiation is larger. The waveguide or horn antenna sensor can be filled with a dielectric material in order to reduce the size of the sensor. In this way, the dimensions of the waveguide or horn can be optimized with regard to the size of the pipe, the interface area between the sensor and the preferred thickness characterization frequency range. The open end of the open-ended circular or rectangular waveguide can alternatively be a completely open end comprising apertures or irises in a shorted wall.

The preferred thickness characterization frequency range depends on the permittivity properties of the dielectric layer. Dielectric materials and fluids typically have a frequency dispersion range wherein the dielectric loss may be high. In this dispersion range, electromagnetic signals are strongly attenuated such that reflections from the interface between the dielectric layer and the backing material is negligible compared to reflections from the interface between the sensor and the dielectric layer. Thus, for thickness estimation, it is preferable to operate the sensor in a frequency range where the dielectric loss is low. The attenuation of electromagnetic signals increases with frequency. Hence, a low frequency operating range may be preferred over a high frequency operating range. As an example, water has maximum dielectric loss around 18 GHz (depending on temperature), and a preferable frequency operating range is below 5 GHz for thickness estimation.

The permittivity in the material characterization frequency range can be estimated from measurements using well-known methods and sensors. The calibration models for estimating permittivity from measured parameters can be experimentally or theoretically based. Examples of measurement principles that can be used for this are reflection coefficient measurements with an open-ended coaxial probe, an open-ended circular or rectangular waveguide, a waveguide horn antenna, or a patch antenna. Other examples of measurement principles are transmission and/or reflection measurements with a coplanar waveguide or other line measurement technique (such as a leaky waveguide). For sensors operated in the material characterization mode, permittivity calculation methods, assuming infinite half-space, can be applied to calculate the permittivity from the measured parameter. If the impedance mismatch is outside the reactive sensitivity depth, the estimated permittivity will be equal to the permittivity of the dielectric layer. If the impedance mismatch is inside the reactive sensitivity depth, simple models such as the empirical relationship for the open-ended coaxial probe described in (Folgerø and Tjomsland, 1996) can be used to account for the finite thickness and to calculate the dielectric layer permittivity from the measured permittivity.

Figure 4A:
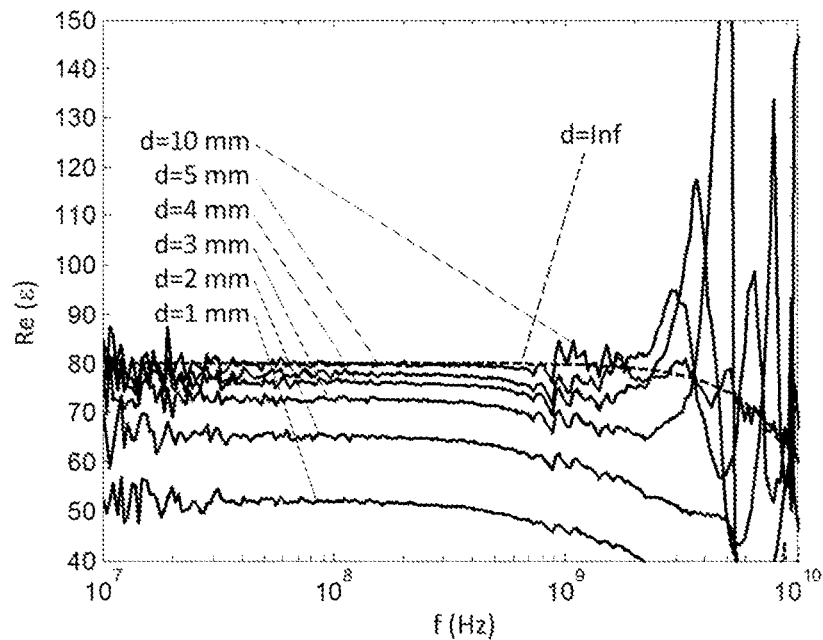
FIG. 4A shows measured relative permittivity (real part) for layers of water.

If a permittivity calculation method assuming an infinite half-space is applied in the thickness characterization frequency range, the estimated permittivity will have a frequency response that deviates from the typical dielectric dispersion (relaxation) behavior. In FIG. 4A, the deviation from the typical behavior is observed as sharp resonance-like variations in the GHz frequency range. The response of the estimated permittivity will depend on the layer thickness, layer permittivity, backing material/fluid permittivity and sensor characteristics (geometry and dimensions). Thus, it is possible to estimate layer thickness if the other influencing parameters (dielectric layer permittivity, backing material permittivity, sensor geometry with dimensions, etc.) are known.

If the impedance mismatch is located in the far field, the thickness of the layer can be calculated from the ringing frequency or by time-of-flight considerations. A known method for measuring the thickness of material layers located in the far field is the short-pulse radar method (aka ground penetrating radar or GPR). Related technologies include near field radar. Short-pulse radar is the electromagnetic analogue to sonic and ultrasonic pulse-echo methods. In this method, a short pulse is transmitted from an antenna and is reflected at interfaces between materials with difference in permittivity (i.e. impedance mismatches). As a first order approximation, the transit time of the reflected pulse is $$\Delta t = \frac{2d\sqrt{\varepsilon'}}{c} \quad (1)$$

where c is the speed of light, $\varepsilon'$ is the real part of the relative permittivity, and d is the thickness of the layer. The permittivity of the material must be known in order to calculate the thickness from the transit time (time-of-flight) measurements. These applications typically use high-efficiency antennas such as horn antennas. The short-pulse radar method, and related radar methods, require that the impedance mismatch is located in the far field of the antenna for the equations to be valid. This requires that the layer is sufficiently thick such that a well-defined wave can build up from the antenna. Thus, these radar methods have a minimum thickness operating range defined by the properties of the pulse (rise time and duration) and the antenna topology.

If the impedance mismatch is within the radiative near field region, more complex relationships occur. Typically, for instance for open-ended coaxial probes, the response will be described by equations with terms including the propagation constant multiplied by the layer thickness ($\gamma$d), where the propagation constant depends on the square root of the complex permittivity. For the fundamental electromagnetic mode, this can be described as $$\gamma_0 d = j\frac{\omega d}{c}\sqrt{\varepsilon} \quad (2)$$

where $\omega$ is the angular frequency, $\varepsilon$ is the complex relative permittivity, d is the layer thickness, c is the speed of light and $j=\sqrt{-1}$ Equations including higher order modes are given in, for instance, equation 21-23 in (Folgerø et al 1996). Thus, if the layer thickness d is to be calculated using equation (2) or similar, the permittivity of the material must be known. For other sensor topologies, such as open-ended rectangular waveguide sensors and horn antennas, other relationships between the measured response and the layer properties exist. See for instance (Ghasr et al., 2008) for a model of an open-ended waveguide radiating into multilayer dielectric structures. However, they all have in common that the measured response depends on both layer thickness and layer permittivity.

The thickness of a dielectric layer can be estimated from theoretical models, models based on numerical simulations, models based on measured data, or combinations of these. The thickness of a dielectric layer can be calculated based on measurements either in the time domain or frequency domain, and the calculation can be done either in the time domain or the frequency domain. Calculations performed in the time domain are typically time-of-flight calculations, but also more sophisticated calculations methods such as, e.g., fitting to advanced models can be applied. Calculations in the frequency domain can be done by analysing ripples in the reflection coefficient directly, but also more sophisticated calculations methods such as, e.g., fitting to advanced models can be applied. All methods for calculating thickness rely on the permittivity of the layer and the backing material/fluid being known in the operating frequency range. Some specific examples of methods for thickness calculations are as follows.

Minimize the error between the measured response and an analytical or empirical model of the sensor system. The measured response can be permittivity, reflection coefficient, transmission coefficient, standing wave pattern, or similar.

Minimize the error between the measured response and a computer-aided numerical model of the sensor system. The measured response can be permittivity, reflection coefficient, transmission coefficient, standing wave pattern, or similar. The computer-aided numerical model can for instance be based on finite-element method, finite time-domain method, or similar.

Time-domain analysis of time-of-flight of reflected pulses or other signals. The time-domain response can either be measured directly in the time domain or obtained by transformation (e.g., inverse Fourier transformation) of a frequency-domain signal.

Analysis of measured frequency response. The frequency response can either be measured directly in the frequency domain or obtained by transformation (e.g. Fourier transformation) of a time-domain signal.

Comparisons of measured responses, with reference measurements carried out on known dielectric layers and backing materials.

Since the permittivity changes with frequency, the permittivity of the dielectric layer must be known in the thickness characterization frequency range in order to calculate the layer thickness by this method. The permittivity in the thickness characterization frequency range can be measured with a sensor operating in a material characterization mode in the same frequency range, or by combining measurements in another frequency range with application knowledge to estimate the permittivity within this range. For the case of open-ended coaxial probes, a single sensor can be applied in material characterization mode in a low frequency range and in thickness characterization mode in the high frequency range, ensuring that both permittivity and layer thickness can be measured with a single sensor.

The thickness estimation methods described above all rely on knowledge of the layer permittivity and backing material/fluid permittivity in the radiating frequency range. It will now be described how these parameters can be found by combining application knowledge with permittivity measurements in the material characterization frequency range. This basis of this inventive method is that the frequency behavior of the permittivity can be modelled, such that the permittivity in one frequency range can be estimated if the permittivity in another frequency range is known.

Figure 3:
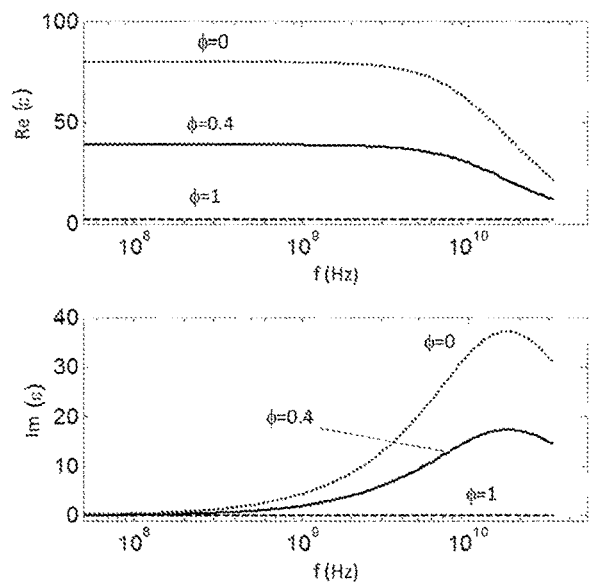
FIG. 3 shows an example of permittivity as a function of frequency for water ($\phi=0$), oil ($\phi=1$) and a 40% oil-in-water emulsion ($\phi=0.4$).

As an example, a wet-gas flow of oil, water and gas is considered. In this case, the liquid layer is a water-in-oil or oil-in-water emulsion. The backing fluid is gas with some small water droplets. Thus, the backing fluid has a relative permittivity close to 1. The permittivity of the liquid layer is given by Bruggeman's equation (here shown for oil-continuous flow)

$$\left(\frac{\varepsilon_w - \varepsilon_m}{\varepsilon_w - \varepsilon_{oil}}\right)\left(\frac{\varepsilon_{oil}}{\varepsilon_m}\right)^{\frac{1}{3}} = 1 - \phi_w \quad (3)$$

where $\varepsilon_m$ is the relative permittivity of the liquid mixture, $\varepsilon_{oil}$ is the relative permittivity of oil, $\varepsilon_w$ is the relative permittivity of water, and $\phi_w$ is the volume fraction of water in liquid. The water permittivity also contains information about the water conductivity. As the permittivity of water and oil changes with frequency, the resulting mixture permittivity will also change with frequency. In a typical application, the water fraction $\phi_w$ can be calculated from permittivity measurements in the MHz range (refer to FIG. 3) by using an appropriate open-ended probe. The mixture's permittivity in the GHz range (refer to FIG. 3) can then be estimated using the a priori known frequency dependency of water and oil, and the calculated water fraction. An open-ended probe with a sensitivity range in the MHz range will typically be radiating in the GHz range, and thus introduce ripples in the measured reflection coefficients. FIG. 4A shows an example of measured permittivity of a water layer for different layer thicknesses. In this example, it is seen that the material characterization frequency range is from approximately 10 MHz to approximately 1 GHz, whereas the thickness characterization frequency range is above 1 GHz for this example. Analysis of these ripples together with knowledge of the mixture's permittivity will then give information about the layer thickness.

In addition to water content, the conductivity of water can also be calculated from the measured permittivity in the material characterization frequency range. This is done by analyzing the imaginary part of the measured permittivity as described in WO2011133046 A1 (EP2561339A1, US20130033272). Further on, the salinity of water can be calculated from the water conductivity if ion composition is known. The example above describes a water-in-oil emulsion. Similar models and relationships exist for oil-in-water emulsion, for three phase mixtures of water, oil and gas, for hydrate particles in liquid, and other mixtures.

Figure 7B:
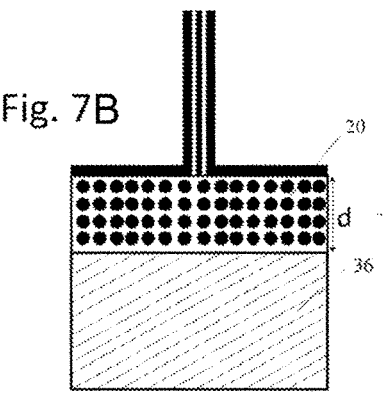
FIG. 7B shows an open-ended coaxial probe measuring a deposition layer 22 backed by liquid 36 in a slugging multiphase flow.
Figure 7A:
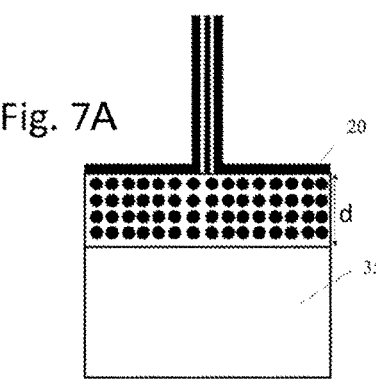
FIG. 7A shows an open-ended coaxial probe measuring a deposition layer 22 backed by gas 35 in a slugging multiphase flow.
Figure 7C:
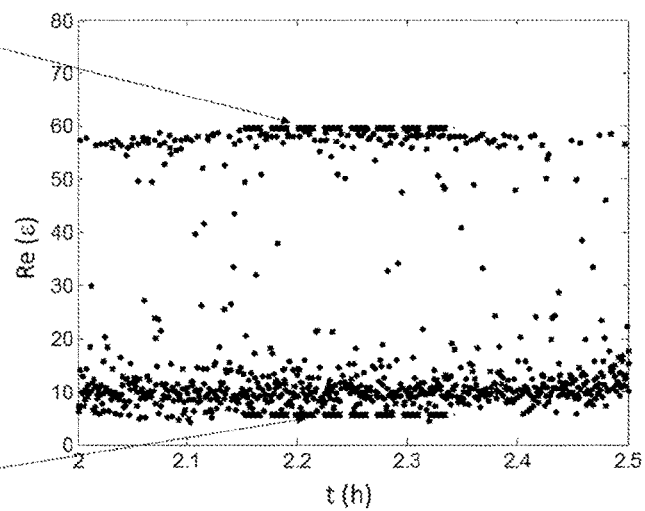
FIG. 7C shows the measured permittivity (real part) at one frequency as a function of time (hours) when measuring a slugging multiphase flow with a deposition layer on the pipe wall.

In the special situation of slug-flow, the method can be applied to extract more information. Consider a multiphase flow of gas and liquid. Under certain flow conditions, such a flow will be wavy or slugging, such that the gas flows as large gas pockets separated by liquid slugs. FIG. 7C shows the measured permittivity at one frequency in the material characterization frequency range as a function of time of such a flow where a deposit 20 is present on the pipe wall, and liquid and gas slugs are flowing through the pipe. If hydrates or other deposits attach to the pipe wall, the following method can be used to characterize both the deposit layer and the liquid flow:

a) During the time period when a large gas pocket or bubble passes the sensor, a deposit in front of the sensor will be backed by gas 35, as shown in FIG. 7A. The method described earlier can then be used to measure the permittivity and layer thickness of the deposit. From the layer permittivity, other properties of the deposit can be estimated using appropriate models, for example, the water and hydrate fraction in the layer, the conductivity of water in the layer, and porosity of the layer.

b) During the time period when liquid passes the sensor, the deposit layer 20 will be backed by liquid 36, as shown in FIG. 7B. As the layer permittivity and thickness now is known, the liquid permittivity can be estimated from the measured permittivity. From the liquid permittivity, other properties of the liquid can be estimated using appropriate models, for example, the water-in-liquid ratio, water conductivity and hydrate fraction.

This inventive method can be generalized to situations where the backing material is changing with time. If the backing material is known in a time period, the method described previously can be used to characterize the dielectric layer and thickness of the layer. The permittivity of another backing material in another time period can then be characterized by using the calculated dielectric layer permittivity and thickness as input parameters. From the calculated backing material permittivity, other parameters can be calculated. The parameters that can be calculated depend on the specific application and what other input parameters are available. Examples of parameters are oil, gas and water content in a multiphase flow, water conductivity, hydrate fraction, etc.

The following describes embodiments of the present invention.

Step 1. Measurements in the Material Characterization Frequency Range:

A sensor made of stainless steel and PEEK as dielectric material will be used as example. The outer radius of the coaxial probe is 10 mm. The permittivity of a material under examination can be calculated using the methods explained in (Folgerø et al, 1996), e.g., the bilinear calibration procedure $$\varepsilon^*_{app} = \frac{A\rho + \varepsilon^*_{ref}}{1 - B\rho} \quad (4)$$

$$\rho = \frac{\Gamma_{ref} - \Gamma_M}{\Gamma_{ref} + \Gamma_M}.$$

Here A, B and $\varepsilon^*_{ref}$ are calibration coefficients that characterize the probe, $\Gamma_{ref}$ is the reflection coefficient for a reference fluid or material, and $\Gamma_M$ is the reflection coefficient for the material under examination. These coefficients are calculated from reference measurements of known standards (in this case known fluids such as, e.g., air, saline water and ethanol). These reference measurements can be done one-time and offline, such that a set of calibration coefficients can be reused when the probe is installed in an application.

Other models than the bilinear calibration procedure can be used to calculate the permittivity (see Folgerø 1996).

Figure 4B:
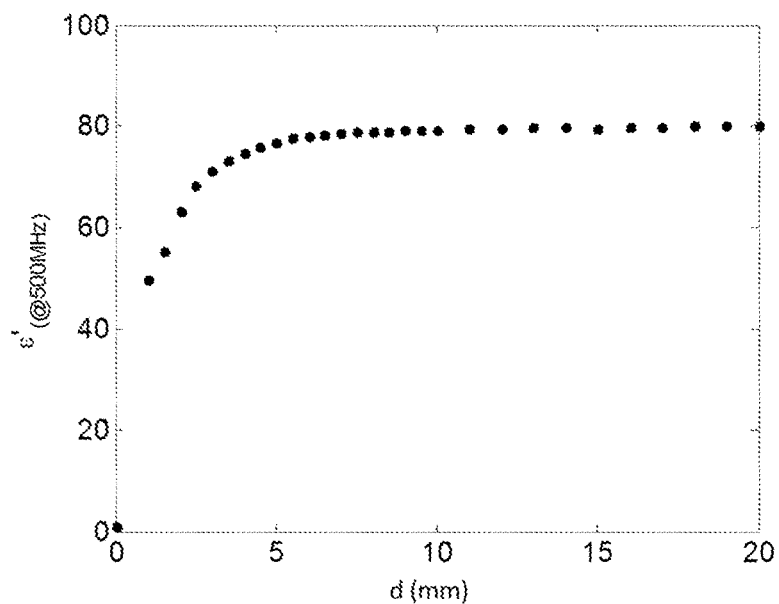
FIG. 4B shows measured relative permittivity (real part) at one frequency in the material characterization frequency range as a function of layer thickness.

FIG. 4A shows the permittivity of water layers with varying thicknesses as a function of frequency estimated using the bilinear calibration procedure. It is seen that the permittivity is estimated well in the frequency range 100 MHz-1 GHz. At lower frequencies, the response is distorted by noise. At higher frequencies (>~1 GHz), reflection from the water-air interface will give ripples in the calculated permittivity. The curve marked d=Inf shows the permittivity of a thick water layer (>20 mm). In this example, it is seen that the material characterization frequency range is from approximately 10 MHz to approximately 1 GHz, whereas the thickness characterization frequency range is above 1 GHz. FIG. 4B shows the measured permittivity of water layers for a frequency in the material characterization frequency range as a function of layer thickness. The measured permittivity is equal to water permittivity for layer thicknesses larger than the reactive sensitivity depth of approximately 5-6 mm.

Typically, the frequency range of the material characterization mode is from 100 MHz to 1 GHz, but frequencies down to 100 kHz and up to 10 GHz may also be applicable, depending on application and sensor geometry. The frequency range for the thickness characterization mode is typically between 1 GHz and 20 GHz, but frequencies down to 100 MHz and up to 60 GHz may be applicable, depending on application and sensor geometry. In some embodiments, the material characterization frequency range may overlap the thickness characterization frequency range. In other embodiments, the thickness characterization frequency range may include the material characterization frequency range.

Step 2. Estimation of Permittivity in the Thickness Characterization Frequency Range The lower frequency limit of the thickness characterization frequency range will depend on probe geometry, layer and backing material thickness, and layer and backing material permittivity. Typically, the lower limiting frequency of the thickness characterization range is between 1 and 10 GHz. When measuring on, for example, wet-gas and slugging multiphase flow, a liquid layer backed by gas will be present in front of the probe. Consider the following special cases:

a) The layer is thicker than the reactive sensitivity depth of the probe

In this situation, the permittivity will be described by an appropriate model. In the case of a water-in-oil emulsion layer backed by gas, Bruggeman's equation (or similar relationships) give the relationship between layer permittivity and water fraction when water and oil permittivities are known. The permittivity of oil and water is known a priori. Water is well characterized, and the permittivity can be calculated if the conductivity and temperature are known (see, e.g., Peyman 2007). The permittivity of oil is known to typically be in the range 2-2.5, which in many cases is accurate enough. Otherwise, it is possible to measure the oil permittivity directly or to give a good estimate based, for example, on hydrocarbon composition (Folgerø, 2012). As the permittivity of oil and water is known, Bruggeman's equation can be applied to calculate the water fraction of the liquid film from the measured permittivity in the material characterization frequency range. If the conductivity of water is not known a priori, Bruggeman's equation can be solved iteratively to estimate both water fraction and water conductivity.

The next step is to apply Bruggeman's equation to estimate the permittivity of the dielectric layer in the thickness characterization frequency range. As the water fraction in the liquid layer is known from the calculations above, the permittivity of the layer in the thickness characterization range is calculated by inserting the a priori known water and oil permittivities in the thickness characterization range into the Bruggeman equation. This permittivity in general will vary with frequency as the water permittivity will vary within the thickness characterization range.

b) The layer is thinner than the reactive sensitivity depth of the probe

In this situation, Bruggeman's equation cannot be used directly to calculate the water fraction, as the measured permittivity differs from the layer permittivity in the material characterization frequency range. However, if the thickness of the layer is assumed to be known, the empirical model or more complex models such as the full-wave model described in (Folgerø et al, 1996) can be used to calculate the layer permittivity. The same method as described can then be used to calculate the permittivity of the layer in the thickness characterization range.

As the thickness of the layer is not known, an iteration method can be used to calculate the thickness and permittivity in this situation. In a first iteration, a layer thickness is assumed. The permittivity in the material characterization range is then calculated as described above, the permittivity in the thickness characterization range is estimated as described in a), and then the thickness of the layer is estimated using the algorithm in Step 3 (below). The estimated thickness from Step 3 is then used as input thickness for next iteration. This is repeated until the estimated thickness in Step 3 converges.

For other cases than water-in-oil emulsions, other models than Bruggeman's equation will be applied to estimate. Another application of particular interest is when a deposit is growing in front of the probe. The deposit can, for example, be wax, scale, asphaltenes, hydrates or a mixture of these. The deposits can also be mixed with fluids such as water, oil or gas. The same approach as described above may be applied here to estimate the permittivities in the thickness characterization range, but the permittivity models used may differ from Bruggeman's. A thorough description of various mixing formulas for permittivity can be found in (Sihvola, 1999).

Deposition layers comprising mixtures of hydrates, water, oil and gas are of particular interest. A specific example is when the dielectric layer comprises hydrate particles in water, forming a slurry. This can be described by a model similar to Bruggeman's equation giving the relation between mixture permittivity, water permittivity, hydrate permittivity and hydrate fraction. This model can be used to calculate the fraction of hydrate particles in water from measurements in the material characterization range (below 1 GHz), as the permittivities of water and hydrate particles are known. The same model can subsequently be used to calculate the layer permittivity in the thickness characterization frequency range by inserting the calculated hydrate fraction, hydrate permittivity and water permittivity as input parameters.

Step 3. Thickness Estimation in the Thickness Characterization Frequency Range

One possible way to determine the thickness from measurements in the thickness characterization mode is described as follows.

Figure 6A:
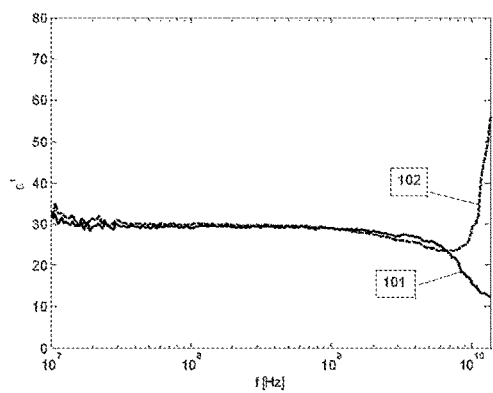
FIG. 6A shows the measured permittivity of a layer with finite thickness 102 and a layer with semi-infinite thickness 101 backed by air.

FIG. 6A shows the measured permittivity of a layer with finite thickness 102 and a semi-infinite thick dielectric 103 in front of an open-ended coaxial probe backed by gas. The permittivity is calculated from the measured coefficient using equation (4). The semi-infinite dielectric is so thick that the sensor is in the material operating mode over the studied frequency range. The dielectric layer is thicker than the reactive sensitivity depth of the sensor, such that the measured permittivity is equal to the layer permittivity in the material characterization frequency range (below approximately 1 GHz). In the radiating frequency range (above approximately 1 GHz), a resonance-like response is observed in the measured permittivity.

In the specific example shown in FIG. 6A, the dielectric layer comprises hydrate particles in water, as discussed above. As the hydrate fraction can be calculated from the permittivity in the material characterization frequency range, and a model of the permittivity as a function of hydrate fraction exist, the layer permittivity in the thickness characterization range (above 1 GHz) can be calculated as described above. This will be equal to the "semi-infinite" response in FIG. 6A.

Figure 6B:
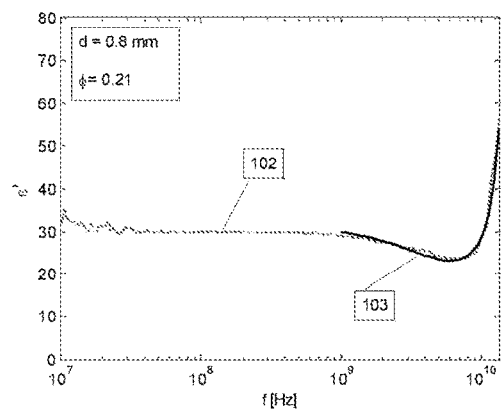
FIG. 6B shows the measured permittivity of a layer with finite thickness 102 and simulated permittivity of a layer with thickness that best fits the measured permittivity 103.

As the layer permittivity and backing fluid permittivity are known, it is possible to apply models, simulations or reference calibration measurements to calculate the layer thickness. Here, a method based on using electromagnetic Finite Element simulation is described. A model of the system comprising a sensor, a dielectric layer and a backing material is simulated. The known material parameters (layer permittivity and backing material permittivity) found as described above are included in the model, and the system is simulated for varying layer thicknesses. The simulated permittivity can be calculated from the simulated reflection coefficients using equation (4). The simulated responses for the varying layer thicknesses are compared to the measured response, and the layer thickness is found from the response that best fits the measured response. FIG. 6B shows an example of measured and simulated permittivity for the thin layer shown in FIG. 6A. Here, the hydrate volume fraction was estimated at 21% from measurements below 1 GHz, and the layer thickness was estimated at 0.8 mm by comparing measurements and simulations above 1 GHz. In this particular example, iterations between Steps 1 to 3 in the calculations algorithm were carried out as the layer thickness was within the reactive region of the sensor.

Figure 6C:
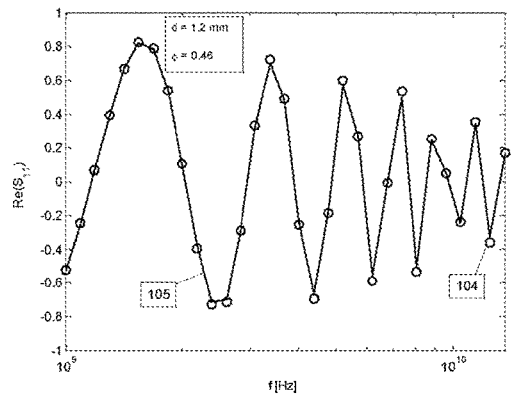
FIG. 6C shows measured reflection coefficient (real part) of a layer with finite thickness 106 and simulated reflection coefficient of a layer with finite thickness 107 that best fits the measured reflection coefficient.
Figure 6D:
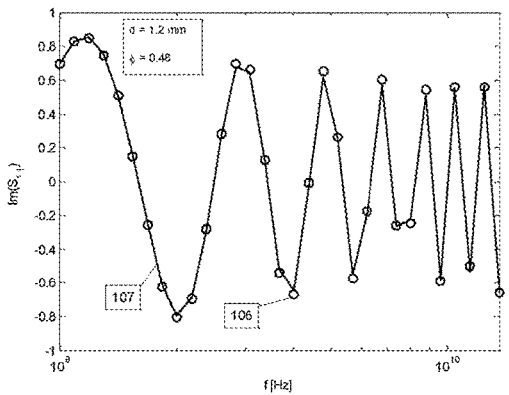
FIG. 6D shows measured reflection coefficient (imaginary part) of a layer with finite thickness 106 and simulated reflection coefficient of a layer with finite thickness 107 that best fits the measured reflection coefficient.

In the example above, the thickness was found by comparing simulated permittivity with measured permittivity. The thickness can also be found by comparing simulated reflection coefficient directly with measured reflection coefficient. FIG. 6C shows a comparison between measured and simulated reflection coefficient for the best fit. Alternatively, the thickness can be found by comparing the measured reflection coefficient or permittivity with analytical or semi-analytical models, for example, the full-wave model described in (Folgerø and Tjomsland, 1996). The comparison can be implemented in an algorithm such that the layer thickness that best fits the measured response is estimated automatically.

Figure 5A:
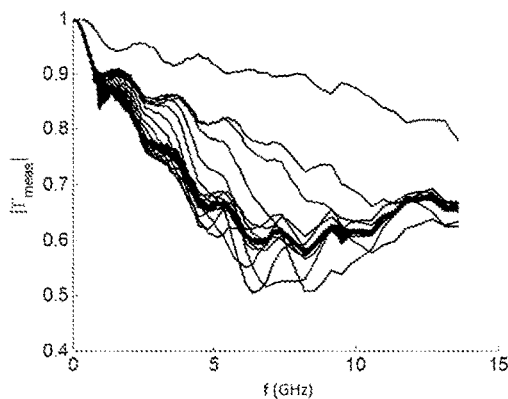
FIG. 5A shows the absolute value of the measured reflection coefficient for various layers.

Another possible way to determine the thickness from swept frequency measurements is described in the following, exemplified in FIG. 5A. First, the following parameters are defined:

$\Gamma_{meas}$: Measured reflection coefficient for a layer with thickness d and permittivity $\varepsilon_1$, and $R(\Gamma_{meas})$: A functional relation of the measured reflection coefficient.

Figure 5B:
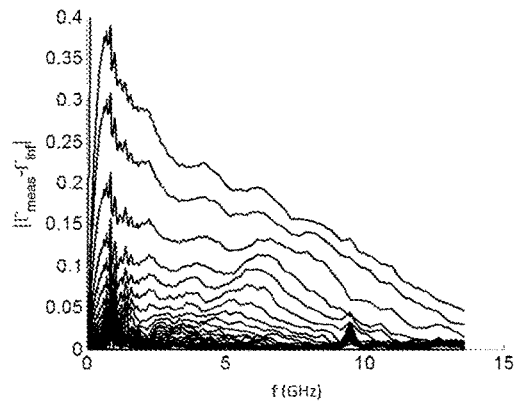
FIG. 5B shows a functional relationship $R(\Gamma_{meas})$ of the measured reflection coefficient for various layers.
Figure 5C:
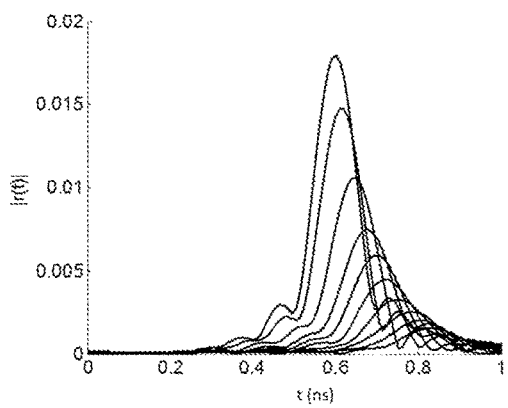
FIG. 5C shows the inverse Fourier transform of the functional relationship $R(\Gamma_{meas})$.
Figure 5D:
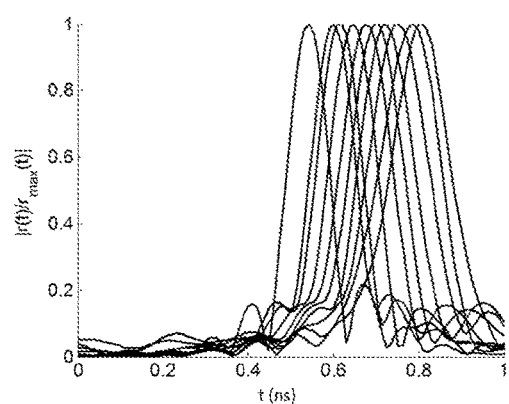
FIG. 5D shows the inverse Fourier transform of the functional relationship $R(\Gamma_{meas})$ normalized to the maximum amplitude, the inverse Fourier transform of the functional relationship ($\Gamma_{meas}$).

The thickness can then be found by the following steps:

1) measuring the reflection coefficient of layer with thickness d and calculating the functional relationship $R(\Gamma_{meas})$ (see the examples in FIGS. 5A and 5B);
2) calculating the inverse Fourier transformation of the functional relationship $R(\Gamma_{meas})$ (see the example in FIG. 5C); and
3) identifying the times $t_i$ corresponding to peaks in the time-domain signal (see the examples in FIG. 5C and FIG. 5D for time-domain and normalized time domain response, respectively).

Figure 5E:
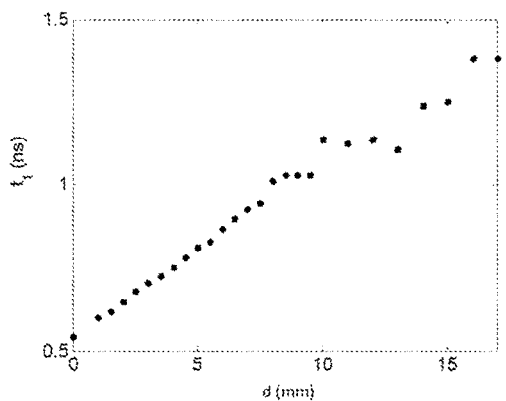
FIG. 5E shows the time corresponding to maximum in the inverse Fourier transform of the functional relationship $R(\Gamma_{meas})$ versus reference thickness.
Figure 5F:
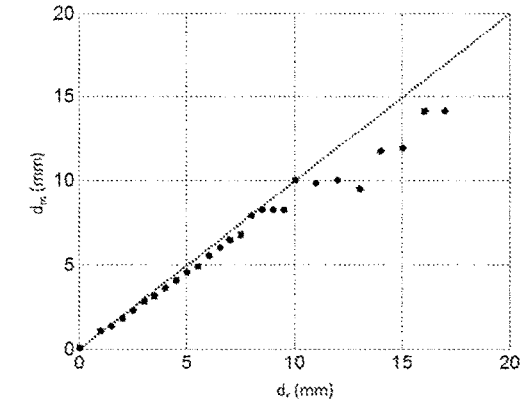
FIG. 5F shows an estimated thickness versus a reference thickness.

The layer thicknesses are calculated from the peak information either by theoretical models, or from empirical relationships. FIG. 5E shows measured times $t_1$ versus reference thicknesses d, and FIG. 5F shows estimated thickness $d_m$ versus reference thickness $d_r$ when using a linear empirical relationship.

An alternative method for estimating the thickness is to analyze the ripples directly in the frequency domain.

Additional information can be extracted by analyzing the permittivity of the layer. Examples are:
  Detection of breakthrough of formation or injection water. This is done by analyzing changes in water conductivity and water-liquid ratio as a function of time. Water conductivity and water-in-liquid ratio can be calculated from the measured permittivity. A preferred installation of the sensor for this example is where the amount of liquid accumulates, for instance in the bottom of the pipe or in bends.
  Detection of hydrate formation onset in bulk. This is done by analyzing the changes in measured permittivity in combination with appropriate models.
  Detection of onset of hydrate deposition on the pipe wall. This is done by analyzing the permittivity and variation in permittivity with time in combination with appropriate models.
  Detection and characterization of slug flow.
  Measurement and characterization of stratified flow. The thickness of liquid layers and content in liquid layers can be calculated by installing a sensor in the bottom of a pipe with stratified flow. The thickness and water content in gas can be estimated by installing an additional sensor in the top of the pipe.

In another preferred embodiment, the sensor system includes an open-ended rectangular or circular waveguide.
In another preferred embodiment, the sensor system includes a waveguide horn antenna.
In another preferred embodiment, the sensor system includes a patch antenna.
In another preferred embodiment, the sensor system includes a leaky waveguide.
In another preferred embodiment, the sensor system includes a coplanar waveguide sensor.
In another preferred embodiment, the sensor system includes a microstrip line sensor.
In another preferred embodiment, the sensor system includes a microwave resonator.
In another preferred embodiment, the sensor system includes several sensors.
In another preferred embodiment, the sensor system includes several sensors attached to the pipeline to characterize the layer or fluid film at several positions.

A number of variations on the present invention can be envisaged. For example:
  Reflection measurements can be done using time-domain methods (Time Domain Reflectometry).
  A modulated signal (e.g., chirp) can be applied as input for the thickness estimation.
  The dielectric layer can be a multi-layer structure, e.g., comprising several dielectric layers. The dielectric layers and backing material may be non-uniform.
  Several sensors or sensor systems can be attached to the pipeline to characterize the layer or fluid film at several positions.
  The system may be applied to other applications than flow inside a pipeline.
  The system can be operated only in the second frequency range, and the permittivity can be calculated from the smoothed response and the thickness from the reflection zeros.
  Reflection and transmission measurement can be combined with the same sensors
  The system can be applied for measurements of layers in a storage tank, such as fluid storage, powder storage, etc.

The invention according to the application finds use in measurements of multiphase flows in pipelines.

REFERENCES

K. Folgerø and T. Tjomsland "Permittivity measurement of thin liquid layers using open-ended coaxial probes" Measurement, Science & Technology, vol. 7, pp 1164-1173, 1996.

K. Folgerø "Coaxial sensors for broad-band complex permittivity measurements of petroleum fluids", Dr. Science. Dissertation, 1996.

K Folgerø, A L Tomren, S Frøyen "Permittivity calculator. Method and tool for calculating the permittivity of oils from PVT data", 30th Int. North Sea Flow Measurement Workshop, St. Andrews, October 2012.

K Folgerø, J Kocbach, "Inline measuring apparatus and method", PCT/NO2011/000134.

K Haukalid, K Folgerø "Measurements of water conductivity in oil continuous emulsions", 10th Int Conf on Electromagnetic Interaction with Water and Moist Substances, Weimar, Germany, Sep. 25-27, 2013.

J. Hilland, "Simple sensor system for measuring the dielectric properties of saline solutions," *Measurement Science and Technology*, vol. 8, no. 8, pp. 901-910, 1997. Ø Isaksen "Device for measurement of coefficient of reflection of high frequency electromagnetic waves in liquids", Ser. No. 19/971,025.

T. Jakobsen and K. Folgerø "Dielectric measurements of gas hydrate formation in water-in-oil emulsions using open-ended coaxial probes" Measurement, Science & Technology, vol. 8, pp 1006-1015, 1997.

Baker-Jarvis J, Janezic M D, Domich P D and Geyer R G 1994 Analysis of an open-ended coaxial probe with lift-off for nondestructive testing IEEE Trans Instrum. Meas. 43 711-18.

Gerardo G. Clemeña "Short-Pulse Radar Methods" in "Handbook on Nondestructive Testing of Concrete," edited by V. M. Malhotra, Nicholas J. Carino.

A. Peyman, C. Gabriel, and E. H. Grant, "Complex permittivity of sodium chloride solutions at microwave frequencies," Bioelectromagnetics, vol. 28, no. 4, pp. 264-274, 2007.

A. H. Sihvola and Institution of Electrical Engineers, *Electromagnetic Mixing Formulas and Applications*. Institution of Electrical Engineers, 1999.

M. T. Ghasr, D. Simms, and R. Zoughi, "Multimodal solution for a waveguide radiating into multilayered structures-Dielectric property and thickness evaluation,"

Instrumentation and Measurement, IEEE Transactions on, vol. 58, no. 5, pp. 1505-1513, 2009.

The invention claimed is:

1. A method for characterizing a dielectric layer with one of, a backing material or fluid behind the dielectric layer, wherein the method comprises:
    measuring a parameter in a first frequency range using a first apparatus, wherein the measured parameter in the first frequency range is at least one of, reflection coefficient, transmission coefficient, and impedance,
    measuring a parameter in a second frequency range using a second apparatus, wherein the measured parameter in the second frequency range is at least one of, reflection coefficient, transmission coefficient, and impedance,
    estimating a permittivity in the first frequency range from the measured parameter in the first frequency range using at least one of, experimentally and theoretically based calibration models,
    estimating a permittivity in the second frequency range by combining an application based model with the estimated permittivity in the first frequency range, wherein the application based model is a model for estimating permittivity as a function of frequency from one of, material or fluid composition, and further comprising estimating the permittivity from at least one of, theoretical models, numerical simulations, and measured data,
    providing an estimate of a thickness of the dielectric layer from the measured parameter in the second frequency range and at least one of, theoretical models, models derived from numerical simulations, and models derived from measured data,
    wherein the first frequency range is a material characterization frequency range wherein reflections from an interface between at least one sensor and the dielectric layer is dominating compared with reflections from an interface between the dielectric layer and the one of, backing material or fluid behind the dielectric layer, and
    wherein the second frequency range is a thickness characterization frequency range wherein reflections from the interface between the dielectric layer and the one of, backing material or fluid interfere with reflections from the interface between the sensor and the dielectric layer.

2. The method according to claim 1, wherein the permittivity in the first frequency range is estimated using the equations $$\varepsilon^*_{app} = \frac{A\rho + \varepsilon^*_{ref}}{1 - B\rho}$$

$$\rho = \frac{\Gamma_{ref} - \Gamma_M}{\Gamma_{ref} + \Gamma_M},$$

where A, B and $\varepsilon^*_{ref}$ are calibration coefficients that characterize the probe, $\Gamma_{ref}$ is the reflection coefficient for a reference fluid or material, and $\Gamma_M$ is the reflection coefficient for the material under examination.

3. The method according to claim 1, wherein the permittivity in the second frequency range is estimated by Bruggeman's equation for oil-continuous flow $$\left(\frac{\varepsilon_W - \varepsilon_m}{\varepsilon_W - \varepsilon_{oil}}\right)\left(\frac{\varepsilon_{oil}}{\varepsilon_m}\right)^{\frac{1}{3}} = 1 - \phi_W,$$

where $\varepsilon_m$ is the relative permittivity of the liquid mixture, $\varepsilon_{oil}$ is the relative permittivity of oil, $\varepsilon_w$ is the relative permittivity of water, $\phi_w$ is the volume fraction of water in liquid.

4. The method according to claim 2, wherein the thickness of the dielectric layer is calculated using one of, a full-wave model and a finite element model, and as inputs, the estimated permittivity in the first frequency range and the estimated permittivity in the second frequency range.

5. The method according to claim 1, further comprising detecting presence of at least one of (a) wax, (b) hydrates, (c) scale, (d) asphaltenes, and (e) deposits, for characterization of layers.

6. The method according to claim 1, further comprising estimating content of at least one of, (a) wax, (b) hydrates, (c) scale, (d) asphaltenes, and (e) deposits, for characterization of layers.

7. The method according to claim 1, further comprising estimating a water-content in the dielectric layer for characterization of layers.

8. The method according to claim 1, further comprising estimating a salinity of water in the dielectric layer for characterization of layers.

9. The method according to claim 1, further comprising estimating a hydrate content in the dielectric layer for characterization of layers.

10. The method according to claim 1, wherein the first frequency range is within 100 kHz to 10 GHz.

11. The method according to claim 1, wherein the first frequency range is within 1 MHz to 1 GHz.

12. The method according to claim 1, wherein the second frequency is in the range 100 kHz to 40 GHz.

13. The method according to claim 1, wherein the second frequency is in the range 1 GHz to 10 GHz.

14. A method for combined characterization of a dielectric layer and one of, a backing material or fluid behind the dielectric layer, wherein the method comprises:
    measuring a parameter in a first frequency range using a first apparatus, wherein the measured parameter in the first frequency range is at least one of, reflection coefficient, transmission coefficient, and impedance,
    measuring a parameter in a second frequency range using a second apparatus, wherein the measured parameter in the second frequency range is at least one of, reflection coefficient, transmission coefficient, and impedance,
    estimating a permittivity in the first frequency range from the measured parameter in the first frequency range using at least one of, experimentally and theoretically based calibration models,
    estimating a permittivity in the second frequency range by combining an application based model with the estimated permittivity in the first frequency range, wherein the application based model is a model for estimating permittivity as a function of frequency from one of, material or fluid composition, and further comprising estimating the permittivity from at least one of, theoretical models, numerical simulations, and measured data,
    providing an estimate of a thickness of the dielectric layer from the measured parameter in the second frequency range and at least one of, theoretical models, models derived from numerical simulations, and (c) models derived from measured data,
    wherein the first frequency range is a material characterization frequency range wherein reflections from an interface between at least one sensor and the dielectric layer is dominating compared with reflections from an interface between the dielectric layer and the one of, backing material or fluid, wherein the second frequency range is a thickness characterization frequency range wherein reflections from the interface between the dielectric layer and the one of, backing material or fluid interfere with reflections from the interface between the sensor and the dielectric layer, characterizing the dielectric layer in a first time period when a permittivity of the fluid or material behind the dielectric layer is known, measuring permittivity in a second time period when the permittivity of the fluid or material behind the dielectric layer is unknown, and estimating the permittivity of the one of, backing material or fluid behind the dielectric layer, from the measurement in the second time period.

15. A method according to claim 14, wherein combined characterization comprises estimating the one of, water content or hydrate content in the dielectric layer and the backing fluid.

16. A system for characterizing a dielectric layer with one of, a backing material or fluid behind the dielectric layer, the system comprising:

a first apparatus for measuring a parameter in a first frequency range, wherein the measured parameter in the first frequency range is at least one of, reflection coefficient, transmission coefficient, and impedance, a second apparatus for measuring a parameter in a second frequency range, wherein the measured parameter in the second frequency range is at least one of, reflection coefficient, transmission coefficient, and impedance, estimating a permittivity in the first frequency range from the measured parameter in the first frequency range using at least one of, experimentally and theoretically based calibration models, estimating a permittivity in the second frequency range by combining an application based model with the estimated permittivity in the first frequency range, wherein the application based model is a model for estimating permittivity as a function of frequency from one of, material or fluid composition, and further comprising estimating the permittivity from at least one of, theoretical models, numerical simulations, and measured data, providing an estimate of a thickness of the dielectric layer from the measured parameter in the second frequency range, and at least one of, theoretical models, models derived from numerical simulations, and models derived from measured data, wherein the first frequency range is a material characterization frequency range wherein reflections from an interface between at least one sensor and the dielectric layer is dominating compared with reflections from an interface between the dielectric layer and the one of, backing material or fluid, and wherein the second frequency range is a thickness characterization frequency range wherein reflections from the interface between the dielectric layer and the one of, backing material or fluid interfere with reflections from the interface between the at least one sensor and the dielectric layer, the at least one sensor measuring the parameter in the first frequency range, and the at least one sensor measuring the parameter in the second frequency range.

17. The system according to claim 16, wherein the at least one sensor measuring the parameter in the first frequency range and the least one sensor measuring the parameter in the second frequency range are the same sensor.

18. The system according to claim 16, wherein the at least one sensor measuring the parameter in the first frequency range and the least one sensor measuring the parameter in the second frequency range are different sensors.

19. The system according to claim 16, wherein the at least one sensor is one of, an open-ended coaxial probe, an open-ended waveguide, an open-ended waveguide horn antenna, or a coplanar waveguide sensor.

20. The method according to claim 14, wherein the permittivity in the first frequency range is estimated using the equations $$\varepsilon^*_{app} = \frac{A\rho + \varepsilon^*_{ref}}{1 - B\rho}$$

$$\rho = \frac{\Gamma_{ref} - \Gamma_M}{\Gamma_{ref} + \Gamma_M},$$

where A, B and $\varepsilon^*_{ref}$ are calibration coefficients that characterize the probe, $\Gamma_{ref}$ is the reflection coefficient for a reference fluid or material, and $\Gamma_M$ is the reflection coefficient for the material under examination.

21. The method according to claim 14, wherein the permittivity in the second frequency range is estimated by Bruggeman's equation for oil-continuous flow $$\left(\frac{\varepsilon_W - \varepsilon_m}{\varepsilon_W - \varepsilon_{oil}}\right)\left(\frac{\varepsilon_{oil}}{\varepsilon_m}\right)^{\frac{1}{3}} = 1 - \phi_W,$$

where $\varepsilon_m$ is the relative permittivity of the liquid mixture, $\varepsilon_{oil}$ is the relative permittivity of oil, $\varepsilon_w$ is the relative permittivity of water, $\phi_w$ is the volume fraction of water in liquid.

22. The method according to claim 21, wherein the thickness of the dielectric layer is calculated using one of, a full-wave model and a finite element model, and as inputs, the estimated permittivity in the first frequency range and the estimated permittivity in the second frequency range.

23. The method according to claim 16, wherein the permittivity in the first frequency range is estimated using the methods using $$\varepsilon^*_{app} = \frac{A\rho + \varepsilon^*_{ref}}{1 - B\rho}$$

$$\rho = \frac{\Gamma_{ref} - \Gamma_M}{\Gamma_{ref} + \Gamma_M},$$

where A, B and $\varepsilon^*_{ref}$ are calibration coefficients that characterize the probe, $\Gamma_{ref}$ is the reflection coefficient for a reference fluid or material, and $\Gamma_M$ is the reflection coefficient for the material under examination.

24. The method according to claim 16, wherein the permittivity in the second frequency range is estimated by Bruggeman's equation for oil-continuous flow $$\left(\frac{\varepsilon_W - \varepsilon_m}{\varepsilon_W - \varepsilon_{oil}}\right)\left(\frac{\varepsilon_{oil}}{\varepsilon_m}\right)^{\frac{1}{3}} = 1 - \phi_W,$$

where $\varepsilon_m$ is the relative permittivity of the liquid mixture, $\varepsilon_{oil}$ is the relative permittivity of oil, $\varepsilon_w$ is the relative permittivity of water, $\phi_w$ is the volume fraction of water in liquid.

25. The method according to claim 24, wherein the thickness of the dielectric layer is calculated using one of, a full-wave model and a finite element model, and as inputs, the estimated permittivity in the first frequency range and the estimated permittivity in the second frequency range.

* * * * *